United States Patent [19]
Soppet et al.

[11] Patent Number: 5,994,506
[45] Date of Patent: Nov. 30, 1999

[54] ADRENERGIC RECEPTOR

[75] Inventors: Daniel R. Soppet, Centreville, Va.; Yi Li, Gaithersburg; Mark D. Adams, North Potomac, both of Md.

[73] Assignee: Human Genome Sciences, Inc., Rockville, Md.

[21] Appl. No.: 09/030,582

[22] Filed: Feb. 25, 1998

Related U.S. Application Data

[60] Division of application No. 08/467,568, Jun. 6, 1995, Pat. No. 5,817,477, which is a continuation-in-part of application No. PCT/US94/00009, Aug. 10, 1994.

[51] Int. Cl.[6] .................................................. C07K 14/705
[52] U.S. Cl. ..................... 530/350; 530/300; 435/69.1; 536/23.5
[58] Field of Search ..................................... 530/350, 300; 435/69.1; 536/23.5

[56] References Cited

U.S. PATENT DOCUMENTS

| | | | |
|---|---|---|---|
| 5,053,337 | 10/1991 | Weinshank et al. | 435/240.2 |
| 5,288,607 | 2/1994 | Emorine et al. | 435/6 |
| 5,607,918 | 3/1997 | Erikssson et al. | 514/12 |
| 5,817,477 | 10/1998 | Soppet et al. | 435/65.1 |

OTHER PUBLICATIONS

Granneman, et al., Molecular Pharmacology, 40:895–899 (1991).
Lomasney, et al., The Journal of Biological Chemistry, 266(10): 6365–6369 (1991).
Fraser, et al., The Journal of Biological Chemistry, 264(20): 11754–11761 (1989).
Milano, et al., Science, 264: 582–586 (1994).
Strader, Cell, 49:855–863 (1987).
Seachrist, L., 264:507–508 (1994).

*Primary Examiner*—Sally P. Teng
*Attorney, Agent, or Firm*—A. Anders Brookes

[57] ABSTRACT

A human adrenergic receptor polypeptide and DNA (RNA) encoding such polypeptide and a procedure for producing such polypeptide by recombinant techniques is disclosed. Also disclosed are agonists for the adrenergic receptor polypeptide which may be used therapeutically to stimulate the adrenergic receptor and antagonist inhibitors against such adrenergic receptor polypeptides and their use therapeutically to antagonize the adrenergic receptor. Also disclosed are diagnostic methods for detecting mutations in the polynucleotides of the present invention and for detecting levels of the soluble polypeptides in samples derived from a host.

14 Claims, 14 Drawing Sheets

FIG. 1A

```
         10                        30                         50
CCCTCCCAGGTtCAAgCAATtcTCCgCCTCGGCCTCTCCAGTAGCTGGACTACAGTCGT
             70                          90                        110
CCAGcATGCTCTGCCCACCCACgCCGAGgTGCACTGACCATGAGCCTCAACTCCCCT
                                                    M  S  L  N  S  S  L
            130                         150                        170
CAGCTGCAGGAAGGAGCTGAGTAATCTCACTGAGGAGGAGGGTGcGAaGGGGCGTCATC
 S  C  R  K  E  L  S  N  L  T  E  E  E  G  G  E  G  A  S  S
            190                         210                        230
ATCACCCAGTTCATCGCCATCATTGTCATCACCATTtTGTCTGCCTGGGaAAACCTGGT
 S  P  S  S  P  S  L  S  S  P  F  L  S  A  W  G  N  L  V
            250                         270                        290
CATCGTGGTCACCTTGTACAAGAAGTCCTACCTCCTCACCCTCAGcAACAAGTTCGTCTT
 I  V  V  T  L  Y  K  K  S  Y  L  L  T  L  S  N  K  F  V  F
            310                         330                        350
CAGCCTGACTCTGTCCAACTTCCTGCTGTCCGTGTTGGTGCTGCCTtTtGTGGTGACGAg
 S  L  T  L  S  N  F  L  L  S  V  L  V  L  P  F  V  V  T  S
            370                         390                        410
CTCCATCCGcCAGGAATGgatCTTTGGTGTAgTGTGGTGCAAcTTCTCTgCCTTCCTCTA
 S  I  R  R  E  W  I  F  G  V  V  W  C  N  F  S  A  L  L  Y
            430                         450                        470
CCTGcTGATCAGCTCTGCCATGCTAACCCTCGGGGTCATTGCCATCGACCGCTACTA
 L  L  I  S  S  A  S  M  L  T  L  G  V  I  A  I  D  R  Y  Y
            490                         510                        530
TGcTGTCCTGTaCCCCATGGTGTaCCCCATGAAGAtCACAGGAACCGGGCTGTGATGGC
 A  V  L  Y  P  M  V  Y  P  M  K  I  T  G  N  R  A  V  M  A
```

FIG. 1B

```
            550                                 570                     590
ACTTGTCTACATCTGGCTTCACTCGCTCCATCGGCCTTGCCACCTGTtGGTTGGTC
 L  V  Y  I  W  L  H  S  L  I  G  C  L  P  P  L  F  G  W  S
   610                                 630                     650
ATCCGTGGAGTATGGCGAGaaCAAATGGCGAGaaCAAATGGATGTGTGGCTTGGCACCGGAGCCTGG
 S  V  E  Y  G  E  N  K  W  M  C  V  A  A  W  H  R  E  P  G
   670                                 690                     710
CtACACGGCCTTCTGGCAGATCTGGTGTGCCCTTTCTGGTCATGCTGGTGTG
 Y  T  A  F  W  Q  I  W  C  A  L  F  P  F  L  V  M  L  V  C
   730                                 750                     770
CTATGGCTtCATCTtcCGCGTGGCCAGGtCAAGGCACGCAAGGTGCACTGTGGCACAGT
 Y  G  F  I  F  R  V  A  R  V  K  A  R  K  V  H  C  G  T  V
   790                                 810                     830
CGTCATCGTGGAGGAGGATGCTCAGAGGACCGGGAGGAAGAACTCCAGCACCTCCACCTC
 V  I  V  E  E  D  A  Q  R  T  G  R  K  N  S  S  T  S  T  S
   850                                 870                     890
CTCTTCAGGgAGgAGGAGGAATGCCTTTCAGGGTGTGGTCGTCTACTCGGCCAACCAGTGCAA
 S  G  R  R  R  N  A  F  Q  G  V  V  Y  S  A  N  Q  C  K
   910                                 930                     950
AGCCCCTCACCATCCCTGGTCCCTCGTGCCTTCATGGTCACCTGGGGCCCCTACAT
 A  L  I  T  I  L  V  V  L  G  A  F  M  V  T  W  G  P  Y  M
   970                                 990                    1010
GGTTGTCATCGCCTCTGAGGCCCTCTGGGGGAAAAGCTCCGTCTCCCCGAGCCTGGAGAC
 V  V  I  A  S  E  A  L  W  G  K  S  S  V  S  P  S  L  E  T
  1030                                1050                    1070
TTGGGCCACATGGCTGTCCTTTGCCAGCGTGTGCCACCCCCTGATCTATGGACTCTG
 W  A  T  W  L  S  F  A  S  A  V  C  H  P  L  I  Y  G  L  W
```

FIG. 1C

```
                                                1130
GAACAAGACAGTTCGCAAAGAACTACTGGGCCATGTGTGCTTTGGGGACCGGTATTATCGGA
 N  K  T  V  R  K  E  L  L  G  M  C  F  G  D  R  Y  Y  R  E
        1150                              1190
ACCATTTGTGCAACGACAGAGGACTTCCAGGCTCTTCAGCATTTCCAACAGGATCACAGA
 P  F  V  Q  R  Q  R  T  S  R  L  F  S  I  S  N  R  I  T  D
   1210                          1250
CCTGGGCCTGTCCCCACACCTCACTGCGCTCATGGCAGGCGGACAGCCCCTGGGCACAG
 L  G  L  S  P  H  L  T  A  L  M  A  G  G  Q  P  L  G  H  S
        1270                            1310
CAGCAGCACGGGGACACTGGCTTCAGCTGCTCCCAGGACTCAGGGACAGATATGATGCT
 S  S  T  G  D  T  G  F  S  C  S  Q  D  S  G  T  D  M  M  L
            1330                         1370
GCTTGAGGACTACACGTCTGATGACAACCCTCCCTCACTGCACTTGCCCACCCAAGAG
 L  E  D  Y  T  S  D  D  N  P  P  S  H  C  T  C  P  P  K  R
        1390                           1430
AAGGAGCTCGGTGACATTTGAGGATGAAGTGGAACAAATCAAAGAAGCTGCCAAGAACTC
 R  S  S  V  T  F  E  D  E  V  E  Q  I  K  E  A  A  K  N  S
            1450                        1490
GATTCTTCATGTGAAAGCTGAAGTCCATAAGTCCTTGGACAGTTACGCCAGCAAGCTTGGC
 I  L  H  V  K  A  E  V  H  K  S  L  D  S  Y  A  A  S  L  A
        1510                           1550
CaAAGCCATTGAGGCCGAAGCCaAAAATCAACTTATTTGGGAGGAGGCTTTgCCAGGGGT
 K  A  I  E  A  E  A  K  I  N  L  F  G  E  E  A  L  P  G  V
```

FIG. 1D

```
                                           1590                                 1610
CTTGGTT  AGCACGGACTGTCCCGGGGGCCGCTTCGGGGGCCGCGAGGCAGCAGAAC
 L V  T  A  R  T  V  P  G  G  G  F  G  G  R  R  G  S  R  T
         1630                         1650                      1670
TCTTGTGAGCCAGAGGCTGCAGTTGCAGAGCATGCGAAGAGGAGATGTTTAgCTgCCGA
 L  V  S  Q  R  L  Q  L  Q  S  I  E  E  G  D  V  L  A  A  E
         1690                         1710                      1730
GCAGAGATGAGGGCCTCAGGGTGCCGTGGGGTGCCCAGCCTGAGAGGCTGGCCCGGGGAGG
 Q  R  *
                     1750                         1770                      1790
AGTTCCCATCACCCGCCTGTgcCGCGGCCCTTGGGAGCATGTCACTGTGTACAGCTGCCAC
                     1810                         1830                      1850
ACACAGGAAGGAGCAGCAGCATCTGGTATGCAgCAGGACAAGGACTGAAAATAATGTC
                     1870                         1890                      1910
TACAGTCCACAGCTTCAGCATTTCCAGAGACCAGATGTGAGCTTCTtTTAGGTCCCAgTG
                     1930                         1950                      1970
AtGGGACCAgAAGCatCTAAAgCAAAAAAAaCCAAAaAAAAtTCTAgAgATGTGtTTG
                     1990                         2010                      2030
TGgCTTTgGGGAGgTGGGGCATGGgAGGACCAgAGGACGAAgGGgTTTGgAAGGAGACCCC
                     2050                         2070                      2090
CACATGCATCATTCCTCCTCTTCACAGTGCTGGgAGTCCAGCCGTGCACTGTGCCAG
                     2110                         2130                      2150
ATgCCTCAGGAGGAGAACCCCTCCCCAGTGTACTGTGAAGGATGAaCACAgaACTTCTTCC
                     2170                         2190                      2210
TAATGAAACGCGACCGTCCTGGTgtCTCTaCATGGTTGATGCCgaCAGTGTGGGACCCTC
```

FIG. 1E

```
         2230                2250                2270
AGttcTaGgAcTGGtCCGCAGaGAAttACCCaGGtGcAGtGCGCTTCGGAGCGGTCCTC
         2290                2310                2330
AgtGGCGgCaCCTGtTGgTGtTaATAGGGAcAGaCACAGGCCCTCTTGcAGtcTgGaCCaC
         2350                2370                2390
CCtgtctacTTCCCCTAcTTAaAAGgTctTgGTattcAAaaGGGAgaaaccacttAtAA
         2410                2430                2450
taGtgaagttggtaGggcaGTACTActcTGTTTcATTTCCAGAATTAAAAAAAAtAAA
         2470
tAttAttCCCTGCGGGCCtGTtA
```

```
S T S - - P - L D I   Majority
                |
               50
S P S S S P S L S S   22.PEP
S T A A V G G L V V   HuAlpha1aR.PEP
S N S T L P Q L D I   HuAlpha1b.PEP
C T Q P P A P V N I   HuAlpha1cR.PEP
- - - - - - - - - -   HuBeta2R.PEP
C - - - - - - L D S   HuH2R.PEP Y F I V S L A V A D   Majority
                |
              100
K F V F S L T L S N   22.PEP
Y F I V N L A V A D   HuAlpha1aR.PEP
Y F I V N L A M A D   HuAlpha1b.PEP
Y Y I V N L A V A D   HuAlpha1cR.PEP
Y F I T S L A C A D   HuBeta2R.PEP
C F I V S L A I T D   HuH2R.PEP S I L S L C V I S I   Majority
                |
              150
S M L T L G V I A I   22.PEP
S I L S L C T I S V   HuAlpha1aR.PEP
S I L S L C A I S I   HuAlpha1b.PEP
S I M G L C I I S I   HuAlpha1cR.PEP
S I E T L C V I A V   HuBeta2R.PEP
S I L N L F M I S L   HuH2R.PEP P L - L G W - - K E   Majority
                |
              200
P L - F G W - - - -   22.PEP
P L - L G W - - K E   HuAlpha1aR.PEP
P L - L G W - - K E   HuAlpha1b.PEP
P L - F G W - - R Q   HuAlpha1cR.PEP
P I Q M H W Y R A T   HuBeta2R.PEP
S I H L G W - - N S   HuH2R.PEP
```

```
V M Y C R V F V V    Majority
            |
           250
V C Y G F I F R V    22.PEP
V M Y C R V Y V V    HuAlpha1aR.PEP
V M Y C R V Y I V    HuAlpha1b.PEP
V M Y C R V Y V V    HuAlpha1cR.PEP
F V Y S R V F Q E    HuBeta2R.PEP
I T Y Y R I F K V    HuH2R.PEP

- - - K G H - - R    Majority
            |
           300
- - - - - - - - R    22.PEP
R S A K G H T F R    HuAlpha1aR.PEP
T K A K G H N P R    HuAlpha1b.PEP
A K T K T H - - -    HuAlpha1cR.PEP
- - - - G H G L R    HuBeta2R.PEP
- - - - - - - - -    HuH2R.PEP G S L F G D L K P    Majority
            |
           350
E A L W G K S S V    22.PEP
G S L F P Q L K P    HuAlpha1aR.PEP
G S L F S T L K P    HuAlpha1b.PEP
G S F F P D F K P    HuAlpha1cR.PEP
H V I Q D N L I R    HuBeta2R.PEP
R G L R G D D A I    HuH2R.PEP

- - L R C Q C R -    Majority
            |
           400
R Y Y R E P F V Q    22.PEP
- - L R C Q C R R    HuAlpha1aR.PEP
- - L G C Q C R G    HuAlpha1b.PEP
- - L R I Q C L -    HuAlpha1cR.PEP
- - L - - - C L -    HuBeta2R.PEP
- - F - C - C R L    HuH2R.PEP
```

Decoration 'Decoration #1': Shaded with solid residues that match the Consensus exactly.

```
      T C - S - S Q D -                  Majority
                     |
                    450
      T G F S C S Q D S                  22.PEP
      - C A P S S G D A                  HuAlpha1aR.PEP
      S C L S G S Q R T                  HuAlpha1b.PEP
      T F Y R I S K T D                  HuAlpha1cR.PEP
      - - - - - - - - -                  HuBeta2R.PEP
      K - - - - - - - -                  HuH2R.PEP P G A X D - - - -                  Majority
                     |
                    500
      E A A K N S I L H                  22.PEP
      P G T P E - - - -                  HuAlpha1aR.PEP
      P G R R G - - - -                  HuAlpha1b.PEP
      R I T V S - - - -                  HuAlpha1cR.PEP
      S D N I D - - - -                  HuBeta2R.PEP
      Q G A T D - - - -                  HuH2R.PEP R S V A - - - - -                  Majority
                     |
                    550
      R T V P G G G F G                  22.PEP
      K S P A C - - - -                  HuAlpha1aR.PEP
      R H V A - - - - -                  HuAlpha1b.PEP
      P S T P S - - L D                  HuAlpha1cR.PEP
                                         HuBeta2R.PEP
                                         HuH2R.PEP Majority 22.PEP
                                         HuAlpha1aR.PEP
                                         HuAlpha1b.PEP
                                         HuAlpha1cR.PEP
                                         HuBeta2R.PEP
                                         HuH2R.PEP
```

ADRENERGIC RECEPTOR

This application is a divisional of U.S. Ser. No. 08/467,568, filed Jun. 6, 1995 now U.S. Pat. No. 5,817,477, which is a continuation-in-part of U.S. Ser. No. PCT/US94/09051 filed Aug. 10, 1994.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor. The transmembrane receptor is a G-protein coupled receptor. More particularly, the 7-transmembrane receptor has been putatively identified as an adrenergic receptor. The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., Pnas, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transductions, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The adrenergic receptors comprise one of the largest and most extensively characterized families within the G-protein coupled receptor "superfamily". This superfamily includes not only adrenergic receptors, but also muscarinic, cholinergic, dopaminergic, serotonergic, and histaminergic receptors. Numerous peptide receptors include glucagon, somatostatin, and vasopressin receptors, as well as sensory receptors for vision (rhodopsin), taste, and olfaction, also belong to this growing family. Despite the diversity of signalling molecules, G-protein coupled receptors all possess a similar overall primary structure, characterized by 7 putative membrane-spanning α helices (Probst et al., 1992). In the most basic sense, the adrenergic receptors are the physiological sites of action of the catecholamines, epinephrine and norepinephrine. Adrenergic receptors were initially classified as either α or β by Ahlquist, who demonstrated that the order of potency for a series of agonists to evoke a physiological response was distinctly different at the 2 receptor subtypes (Ahlquist, 1948). Functionally, α adrenergic receptors were shown to control vasoconstriction, pupil dilation and uterine inhibition, while β adrenergic receptors were implicated in vasorelaxation, myocardial stimulation and bronchodilation (Regan et al., 1990). Eventually, pharmacologists realized that these responses resulted from activation of several distinct adrenergic receptor subtypes. β adrenergic receptors in the heart were defined as $β_1$, while those in the lung and vasculature were termed $β_2$ (Lands et al., 1967).

α Adrenergic receptors, meanwhile, were first classified based on their anatomical location, as either pre or post-synaptic ($α_2$ and $α_1$, respectively) (Langer et al., 1974). This classification scheme was confounded, however, by the presence of $α_2$ receptors in distinctly non-synaptic locations, such as platelets (Berthelsen and Pettinger, 1977). With the development of radioligand binding techniques, α adrenergic receptors could be distinguished pharmacologically based on their affinities for the antagonists prazosin or yohimbine (Stark, 1981). Definitive evidence for adrenergic receptor subtypes, however, awaited purification and molecular cloning of adrenergic receptor subtypes. In 1986, the genes for the hamster $β_2$ (Dickson et al., 1986) and turkey $β_1$ adrenergic receptors (Yarden et al., 1986) were cloned and sequenced. Hydropathy analysis revealed that these proteins contain 7 hydrophobic domains similar to rhodopsin, the receptor for light. Since that time the adrenergic receptor family has expanded to include 3 subtypes of β receptors (Emorine et al., 1989), 3 subtypes of $α_1$ receptors (Schwinn et al., 1990), and 3 distinct types of $β_2$ receptors (Lomasney et al., 1990).

The $α_2$ receptors appear to have diverged rather early from either β or $α_1$ receptors. The $α_2$ receptors have been broken down into 3 molecularly distinct subtypes termed $α_2C2$, $α_2C4$, and $α_2C10$ based on their chromosomal location. These subtypes appear to correspond to the pharmacologically defined $α_{2B}$, $α_{2C}$, and $α_{2A}$ subtypes, respectively (Bylund et al., 1992). While all the receptors of the adrenergic type are recognized by epinephrine, they are pharmacologically distinct and are encoded by separate genes. These receptors are generally coupled to different second messenger pathways that are linked through G-proteins. Among the adrenergic receptors, $β_1$ and $β_2$ receptors activate the adenylate cyclase, $α_2$ receptors inhibit adenylate cyclase and $α_1$ receptors activate phospholipase C pathways, stimulating breakdown of polyphosphoinositides (Chung, F. Z. et al., J. Biol. Chem., 263:4052 (1988)). $α_1$ and $α_2$ adrenergic receptors differ in their cell activity for drugs.

In accordance with one aspect of the present invention, there are provided novel polypeptides which have been putatively identified as adrenergic receptors, as well as fragments, analogs and derivatives thereof. The polypeptides of the present invention are of human origin.

In accordance with another aspect of the present invention, there are provided polynucleotides (DNA or RNA) which encode such polypeptides.

In accordance with a further aspect of the present invention, there is provided a process for producing such polypeptides by recombinant techniques.

In accordance with yet a further aspect of the present invention, there are provided antibodies against such polypeptides.

In accordance with another embodiment, there is provided a process for using the receptor to screen for receptor antagonists and/or agonists and/or receptor ligands.

In accordance with still another embodiment of the present invention there is provided a process of using such agonists for therapeutic purposes, for example, to treat upper respiratory conditions.

In accordance with another aspect of the present invention there is provided a process of using such antagonists for treating hypertension.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A, 1B, 1C, 1D and 1E, collectively, show the cDNA sequence (SEQ ID NO:1) and the corresponding deduced amino acid sequence (SEQ ID NO:2) of the G-protein coupled receptor of the present invention. The standard one-letter abbreviation for amino acids is used.

Figure 2A1:
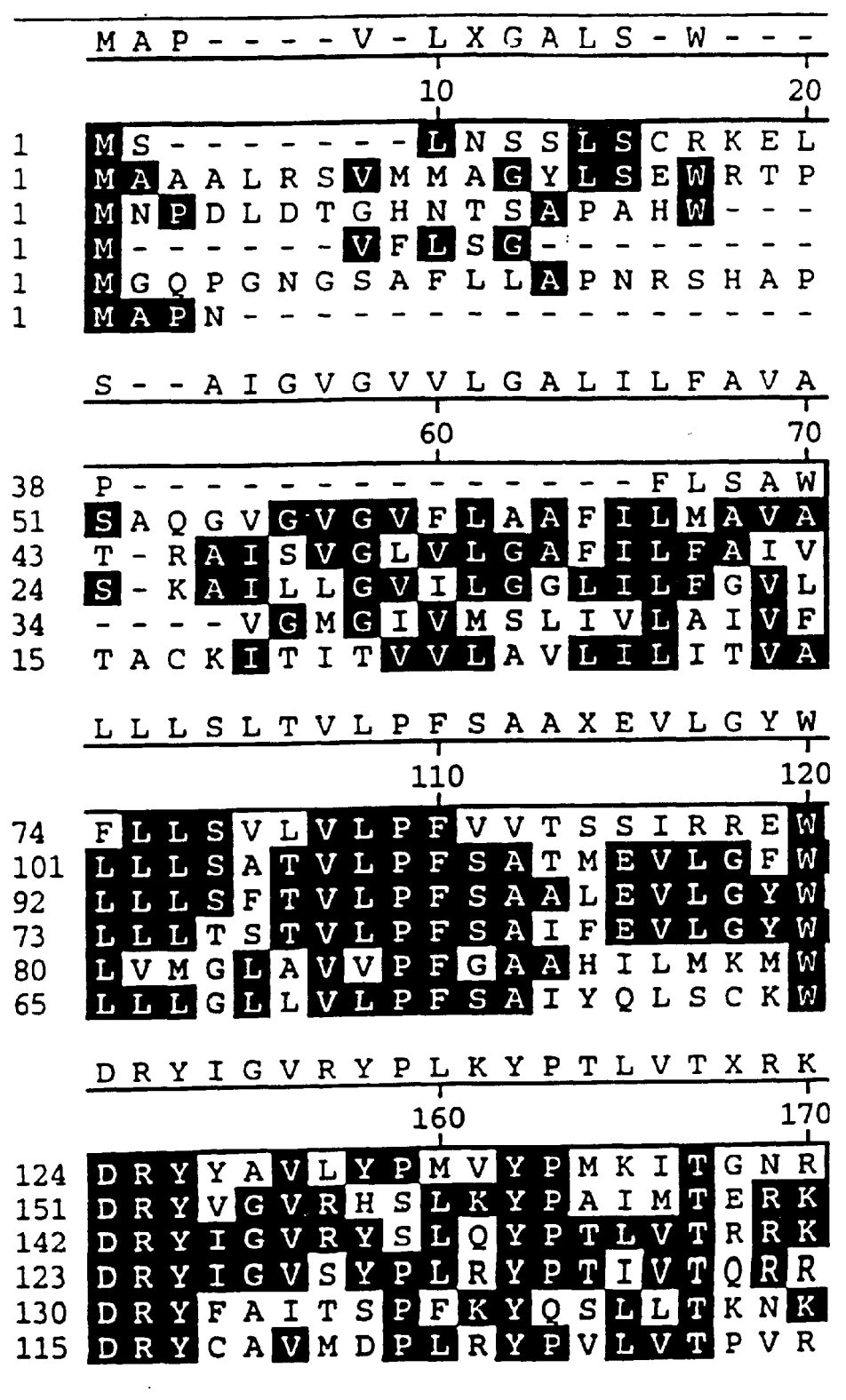
Figure 2A2:
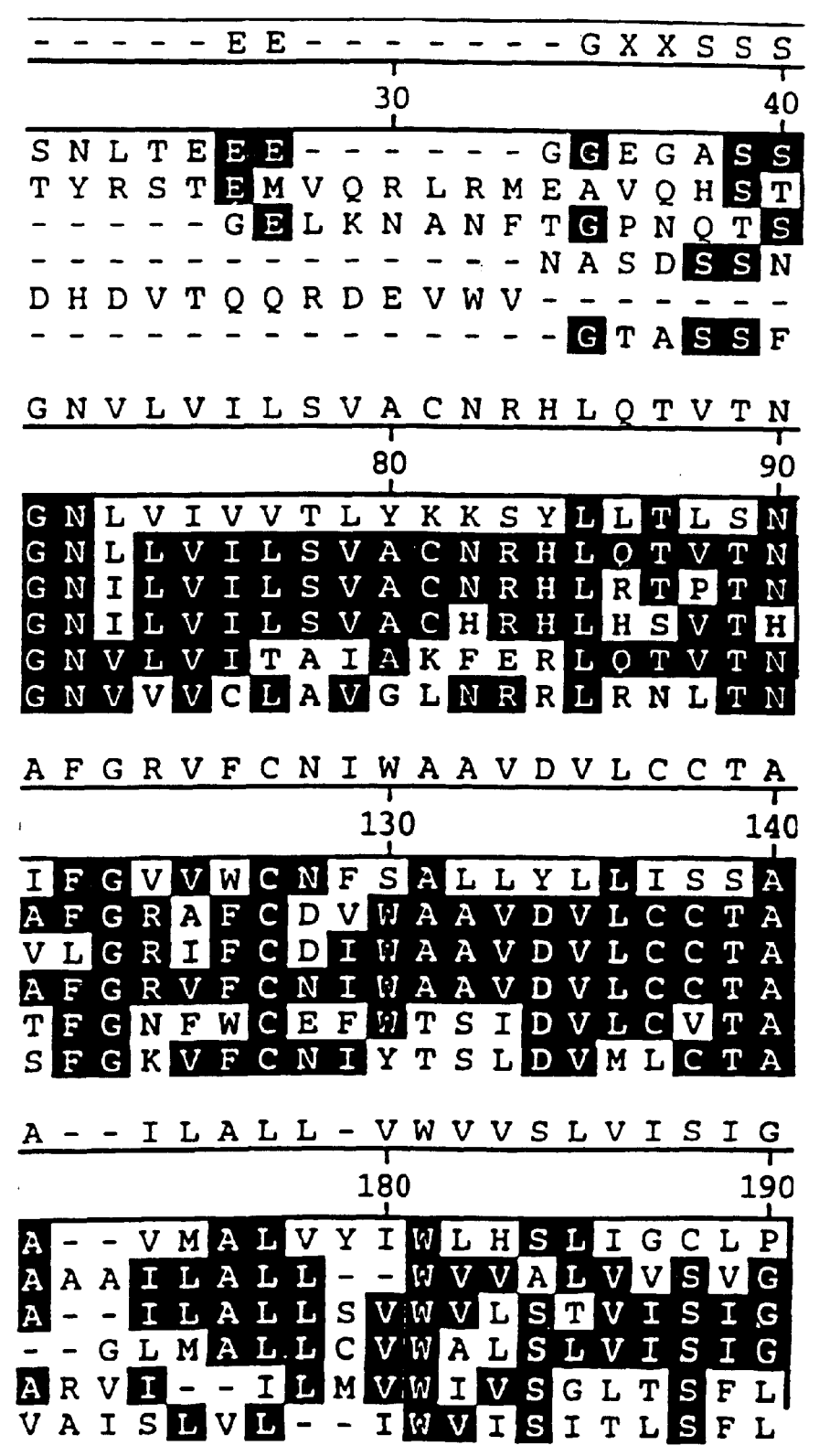
Figure 2B1:
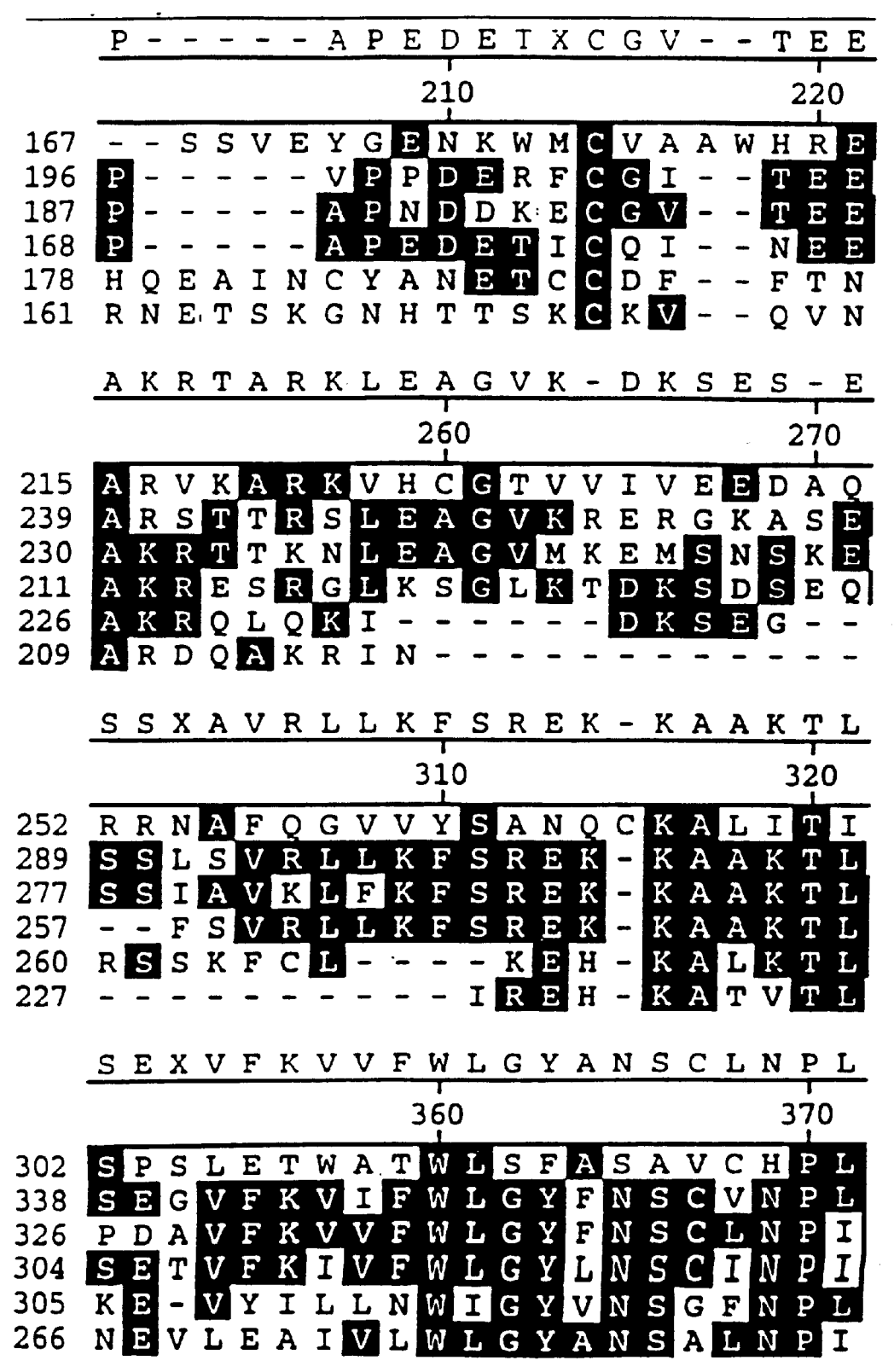
Figure 2B2:
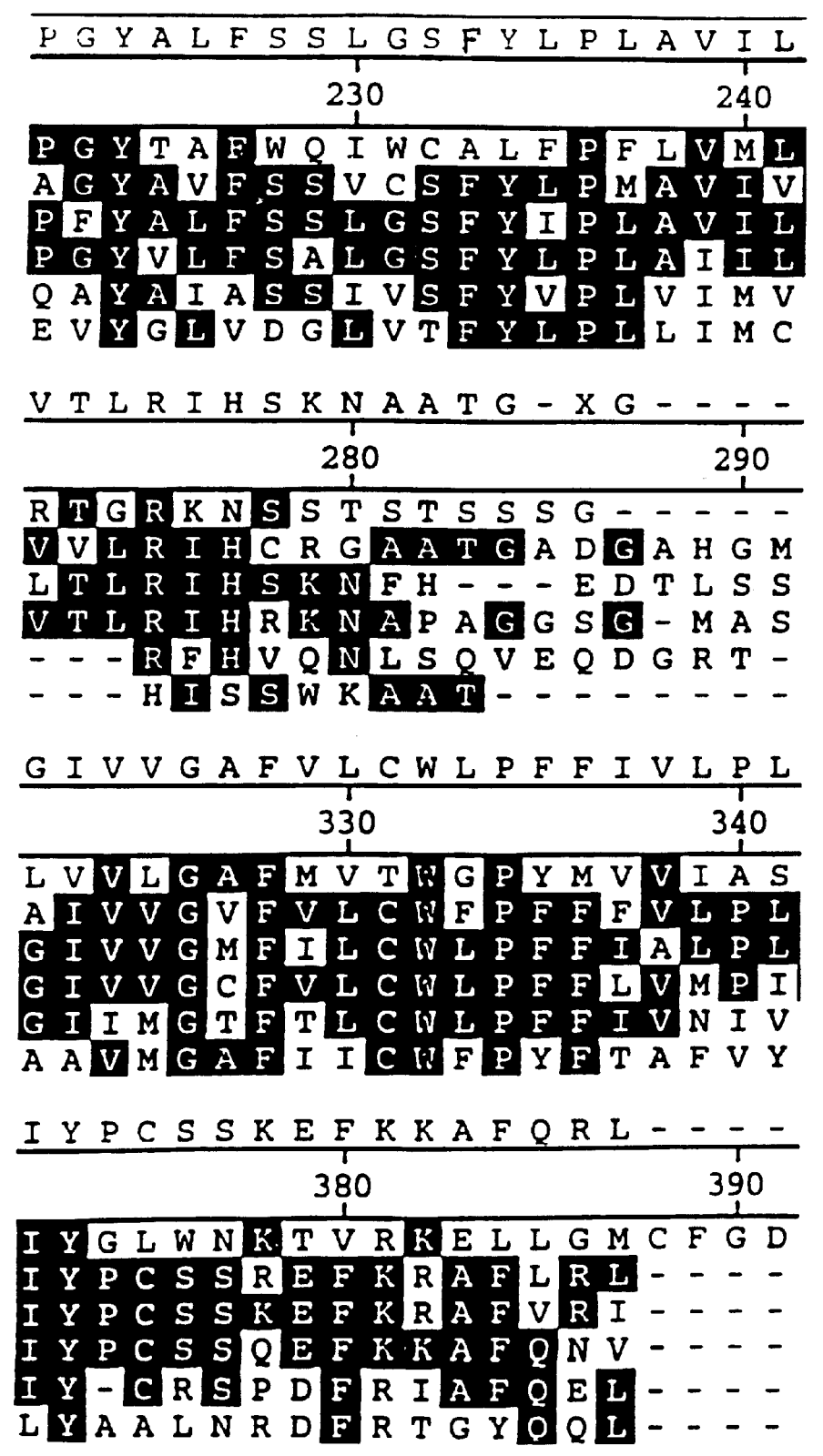
Figure 2C1:
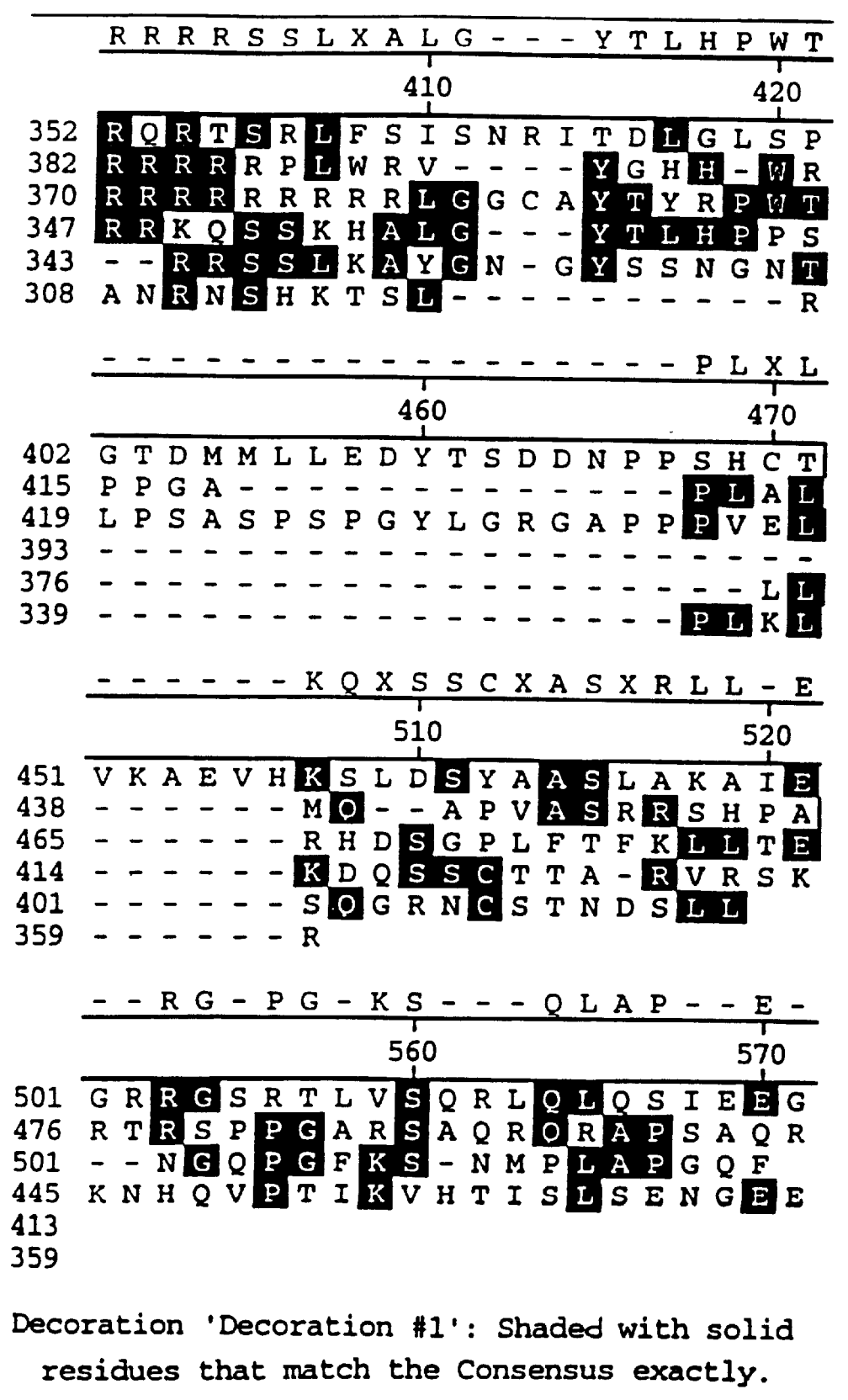
Figure 2C2:
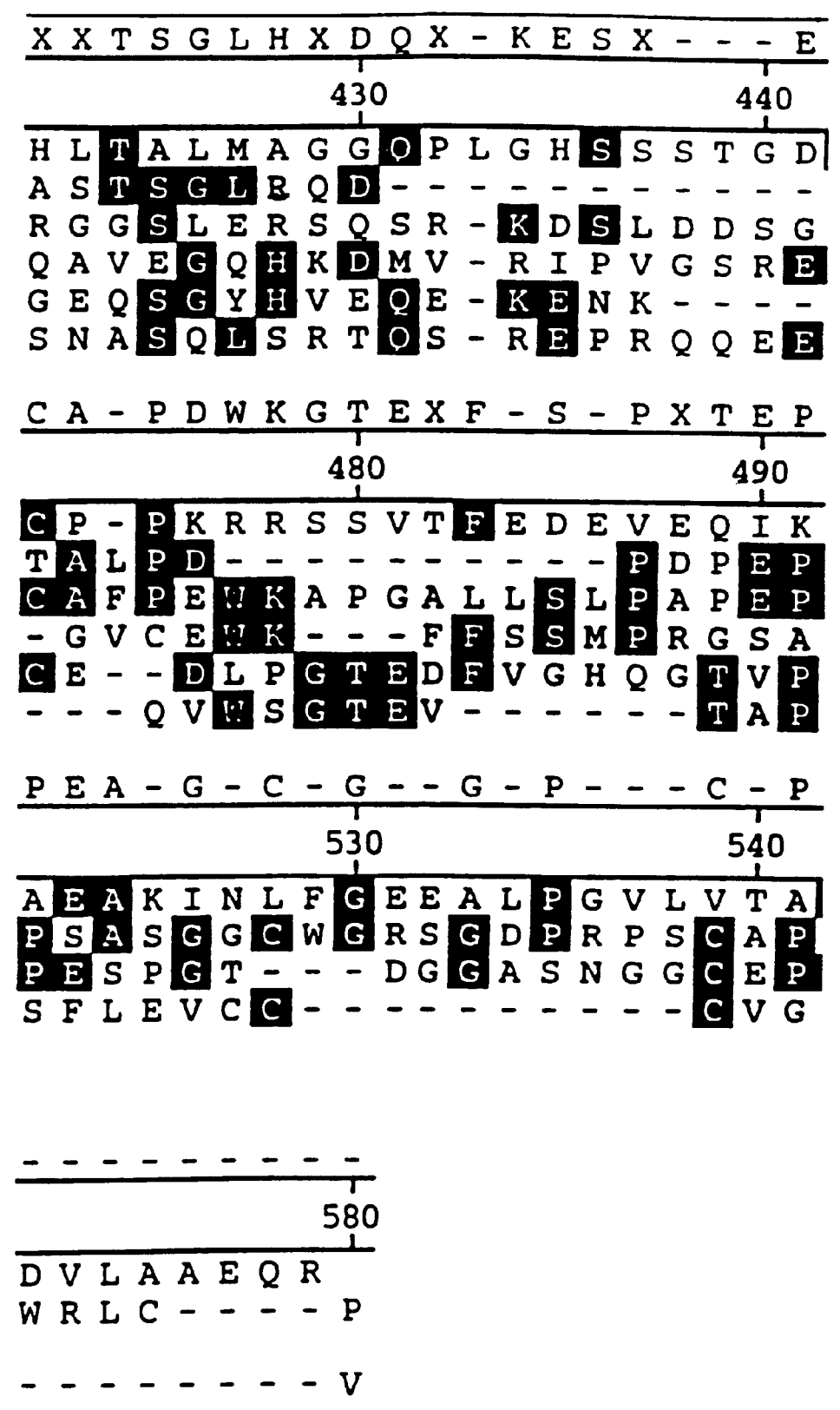

FIGS. 2A1–2A3, 2B1–2B3 and 2C1–2C3, collectively, are an amino acid alignment of the G-protein coupled receptor of the present invention and adrenergic receptors from various species of animals. Faded areas are those areas which match with the other amino acid sequences in the figure. The comparative polypeptide sequences are represented by one-letter amino acid codes and each comparative row has five sets of lines representing the five amino acid sequences SEQ ID NOS: 9–13, respectively.

It should be pointed out that sequencing inaccuracies are a common problem which occurs in polynucleotide sequences. Accordingly, the sequence of the drawing is based on several sequencing runs and the sequencing accuracy is considered to be at least 97%.

In accordance with an aspect of the present invention, there is provided an isolated nucleic acid (polynucleotide) which encodes for the mature polypeptide having the deduced amino acid sequence of FIGS. 1A, 1B, 1C, 1D, and 1E, collectively, (SEQ ID NO:2) or for the mature polypeptide encoded by the cDNA of the clone deposited as ATCC Deposit No. 75822 on Jun. 24, 1994.

The ATCC number referred to above is directed to a biological deposit with the ATCC, 10801 University Boulevard, Manassas, Va. 20110-2209. The strain is being maintained under the terms of the Budapest Treaty and will be made available to a patent office signatory to the Budapest Treaty.

A polynucleotide encoding a polypeptide of the present invention may be found in the brain, lung, pancreas and kidney. The polynucleotide of this invention was discovered in a cDNA library derived from a human infant brain. It is structurally related to the α1 adrenergic receptor family. It contains an open reading frame encoding a protein of 529 amino acid residues. The protein exhibits the highest degree of homology to $\alpha_{1c}$ at the nucleotide sequence level and $\alpha_{1B}$ at the amino acid level with 30% identity and 47% similarity over a 500 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A, 1B, 1C, and 1E, collectively, (SEQ ID NO:1) or that of the deposited clone or may be a different coding sequence which coding sequence, as a result of the redundancy or degeneracy of the genetic code, encodes the same mature polypeptide as the DNA of FIGS. 1A, 1B, 1C, 1D, and 1E, collectively (SEQ ID NO:1) or the deposited cDNA.

The polynucleotide which encodes for the mature polypeptide of FIGS. 1A, 1B, 1C, 1D and 1E, collectively, (SEQ ID NO:2) or for the mature polypeptide encoded by the deposited cDNA may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A, 1B, 1C, 1D, and 1E, collectively, (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A, 1B, 1C, 1D, and 1E, collectively, (SEQ ID NO:2) or the same mature polypeptide encoded by the cDNA of the deposited clone as well as variants of such polynucleotides which variants encode for a fragment, derivative or analog of the polypeptide of FIGS. 1A, 1B, 1C, 1D, and 1E, collectively, (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A, 1B, 1C, 1D, and 1E, collectively, (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the receptor polypeptide which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A, 1B, 1C, 1D, and 1E collectively, (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a receptor polypeptide which has the deduced amino acid sequence of FIGS. 1A, 1B, 1C, 1D, and 1E collectively, (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A, 1B, 1C, 1D, and 1E collectively, (SEQ ID NO:2) or that encoded by the deposited cDNA, means a polypeptide which either retains substantially the same biological function or activity as such polypeptide, i.e. functions as a receptor, or retains the ability to bind the ligand for the receptor even though the polypeptide does not function as a G-protein coupled receptor, for example, a soluble form of the receptor.

The polypeptide of the present invention may be a recombinant polypeptide, a natural polypeptide or a synthetic polypeptide, preferably a recombinant polypeptide.

The fragment, derivative or analog of the polypeptide of FIGS. 1A, 1B, 1C, 1D, and 1E collectively, (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which are employed for purification of the mature polypeptide or a proprotein sequence or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "gene" means the segment of DNA involved in producing a polypeptide chain; it includes regions preceding and following the coding region "leader and trailer" as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.\ coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.\ coli,$ Streptomyces, Salmonella typhimurium; fungal cells, such as yeast; insect cells such as Drosophila and Spodoptera Sf9; animal cells such as CHO, COS or Bowes melanoma; adenovirus; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The G-protein coupled receptor of the present invention may be employed in a process for screening for antagonists and/or agonists for the receptor.

In general, such screening procedures involve providing appropriate cells which express the receptor on the surface thereof. In particular, a polynucleotide encoding the receptor of the present invention is employed to transfect cells to thereby express the G-protein coupled receptor. Such transfection may be accomplished by procedures as hereinabove described.

One such screening procedure involves the use of the melanophores which are transfected to express the G-protein coupled receptor of the present invention. Such a screening technique is described in PCT WO 92/01810 published Feb. 6, 1992.

Thus, for example, such assay may be employed for screening for a receptor antagonist by contacting the melanophore cells which encode the G-protein coupled receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, potential agonists or antagonists may be contacted with a cell which expresses the G-protein coupled receptor and a second messenger response, e.g. signal transduction or pH changes, may be measured to determine whether the potential agonist or antagonist is effective.

Another such screening technique involves introducing RNA encoding the G-protein coupled receptor into xenopus oocytes to transiently express the receptor. The receptor oocytes may then be contacted in the case of antagonist screening with the receptor ligand and a compound to be screened, followed by detection of inhibition of a calcium signal.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

In general, antagonists for G-protein coupled receptors which are determined by screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

A potential antagonist is an antibody, or in some cases an oligonucleotide, which binds to the G-protein coupled receptor but does not elicit a second messenger response such that the activity of the G-protein coupled receptor is prevented. Potential antagonists also include proteins which are closely related to the ligand of the G-protein coupled receptor, i.e. a fragment of the ligand, which have lost biological function and when binding to the G-protein coupled receptor, elicit no response.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251:1360 (1991)), thereby preventing transcription and the production of G-protein coupled receptors. The antisense RNA oligonucleotide hybridizes to the mRNA in vivo and blocks translation of the mRNA molecule into the G-protein coupled receptors (antisense —Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptors.

Another potential antagonist is a small molecule which binds to the G-protein coupled receptor, making it inaccessible to ligands such that normal biological activity is prevented. Examples of small molecules include but are not limited to small peptides or peptide-like molecules.

Potential antagonists also include a soluble form of a G-protein coupled receptor, e.g. a fragment of the receptor, which binds to the ligand and prevents the ligand from interacting with membrane bound G-protein coupled receptors.

The G-protein coupled receptor of the present invention has been putatively identified as an adrenergic receptor. This identification has been made as a result of amino acid sequence homology.

The antagonists may be used to treat hypertension by controlling β-adrenergic receptors from stimulating cardiac contractility and lowering heart rate. The antagonists may also be used to prevent vasoconstriction controlled by α-adrenergic receptors. The antagonists may be employed in a composition with a pharmaceutically acceptable carrier, e.g., as hereinafter described.

The agonists identified by the screening method as described above, may be employed to stimulate the α-adrenergic receptor for the treatment of upper respiratory conditions, e.g. allergic rhinitis, hay fever, acute coryza and sinusitis. Stimulating the α-adrenergic receptors constricts the nasal mucosal blood vessels, lessening secretions, and edema. α-adrenergic receptors also control pupil dilation and uterine inhibition, therefore, the agonists may also be used to stimulate those actions.

β-Adrenergic receptors mediate vasorelaxation. Stimulating β-adrenergic receptors by the administration of an agonist may be used to treat bronchial asthma by causing bronchial smooth muscle relaxation and modulating mediator release, at least in part by stimulating the adenylate cyclase-cAMP system. Stimulating β-adrenergic receptors and consequent vasorelaxation may also be used to treat coronary artery disease, atherosclerosis and arteriosclerosis.

The adrenergic receptor and antagonists or agonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the compounds of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The adrenergic receptor polypeptides and antagonists or agonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CKV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

This invention also provides a method of detecting expression of a receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a receptor polypeptide of the present invention, by low stringency cross hybridization, or by identifying receptors that interact with related natural or synthetic ligands and or elicit similar behaviors after genetic or pharmacological blockade of the receptor polypeptides of the present invention.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., calorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA*, 85:4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to receptor proteins. Unattached reporter antibody is then washed out. Peroxidase substrates are then added to the dish and the amount of color developed in a given time period is a measurement of the amount of receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases.

For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Adrenergic Receptor

The DNA sequence encoding the adrenergic receptor, ATCC # 75822, is initially amplified using PCR oligonucleotide primers corresponding to the 5' and 3' sequences of the processed protein (minus the signal peptide sequence) and the vector sequences 3' to the adrenergic receptor gene. Additional nucleotides corresponding to the adrenergic receptor coding sequence were added to the 5' and 3' sequences respectively. The 5' oligonucleotide primer has the sequence 5' CCCACCCCACGCCGAGGTGCA GGTG-CAGGATCCATGAGCCTCAAC 3' (SEQ ID NO:3) contains a BamHI restriction enzyme site (bold) followed by 9 nucleotides of the adrenergic receptor coding sequence starting from the presumed terminal amino acid of the processed protein codon. The 3' sequence 5' CAGC-CCCACGGCACCCTCTAGACC TCATCTCTGCTCG-GCAGCR 3' (SEQ ID NO:4) contains complementary sequences to an XbaI site and is followed by 21 nucleotides of the adrenergic receptor coding sequence. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with BamHI and XbaI. The amplified sequences were ligated into pQE-9 and were inserted in frame with the sequence encoding for the histidine tag and the RBS. The ligation mixture was then used to transform E. coli strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized adrenergic receptor protein was purified from this solution by chromatography on a Nickel-Chelate column under conditions that allow for tight binding by proteins containing the 6-His tag (Hochuli, E. et al., J. Chromatography 411:177–184 (1984)). The adrenergic receptor protein was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Expression of Recombinant Adrenergic Receptor in COS Cells

The expression of plasmid, pAdrenergic Receptor HA is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire adrenergic receptor precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding the adrenergic receptor, ATCC # 75822, was constructed by PCR on the original EST cloned using two primers: the 5' primer 5' CCCAC-CCCACGCCGGGATCCACTGACCATG 3' (SEQ ID NO:5) contains a BamHI site followed by 10 nucleotides of sequence ending at the initiation codon; the 3' sequence 5' CCGCTCGA GCCTTCAAGCGTAGTCTGGGACGTCG-TATGGGTATCTCTGCTCGGCAGC 3' (SEQ ID NO:6) contains complementary sequences to an EcoRI site, translation stop codon, HA tag and the last 21 nucleotides of the adrenergic receptor coding sequence coding sequence (not including the stop codon). Therefore, the PCR product contains a BAMHI site, coding sequence followed by HA tag fused in frame, a translation termination stop codon next to the HA tag, and an EcoRI site. The PCR amplified DNA fragment and the vector, pcDNAI/Amp, were digested with BamHI and EcoRI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant adrenergic receptor protein, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the adrenergic receptor HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Cloning and Expression of Adrenergic Receptor using the Baculovirus Expression System The DNA sequence encoding the full length adrenergic receptor protein, ATCC # 75822, was amplified using PCR oligonucleotide primers corresponding to the 5' and 3' sequences of the gene:

The 5' primer has the sequence 5' CCCACCC CACGC-CGGGATCCACTGACCATG 3' (SEQ ID NO:7) and contains a BamHI restriction enzyme site (in bold) followed by 10 nucleotides resembling an efficient signal for the initiation of translation in eukaryotic cells (J. Mol. Biol. 1987, 196, 947–950, Kozak, M.), the initiation codon for translation "ATG" is underlined).

The 3' primer has the sequence 5' CAGCCCCACG-GCACCCTCTAGACCTCATCTCTGCTCGGCAGCT 3' (SEQ ID NO: 8) and contains the cleavage site for the restriction endonuclease XbaI and 16 nucleotides complementary to the 3' non-translated sequence of the adrenergic receptor gene. The amplified sequences were isolated from a 1% agarose gel using a commercially available kit ("Geneclean," BIO 101 Inc., La Jolla, Calif.). The fragment was then digested with the endonucleases BamHI and XbaI and purified again on a 1% agarose gel. This fragment is designated F2.

The vector pRG1 (modification of pVL941 vector, discussed below) is used for the expression of the adrenergic receptor protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and XbaI. The polyadenylation site of the simian virus (SV)40 is used for efficient polyadenylation. For an easy selection of recombinant viruses the beta-galactosidase gene from E. coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and XbaI and then dephosphorylated using calf intestinal phosphatase by procedures known in the art. The DNA was then isolated from a 1% agarose gel. This vector DNA is designated V2.

Fragment F2 and the dephosphorylated plasmid V2 were ligated with T4 DNA ligase. E. coli XL1Blue cells were then transformed and bacteria identified that contained the plasmid (pBacAdrenergic Receptor) with the adrenergic receptor gene using the enzymes BamHI and XbaI. The sequence of the cloned fragment was confirmed by DNA sequencing.

5 μg of the plasmid pBacAdrenergic receptor were cotransfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

μg of BaculoGold™ virus DNA and 5 μg of the plasmid pBacAdrenergic Receptor were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells and blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-Adrenergic Receptor at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

---

What is claimed is:

1. An isolated polypeptide comprising at least 50 contiguous amino acid residues of SEQ ID NO:2.

2. The isolated polypeptide of claim 1 comprising the amino acid sequence shown as residues 2 to 529 in SEQ ID NO:2.

3. The isolated polypeptide of claim 2 comprising the amino acid sequence shown as residues 1 to 529 in SEQ ID NO:2.

4. The isolated polypeptide of claim 3 consisting of the amino acid sequence shown as residues 1 to 529 in SEQ ID NO:2.

5. The isolated polypeptide of claim 1 further comprising a heterologous amino acid sequence.

6. An isolated polypeptide comprising at least 50 contiguous amino acid residues of the polypeptide encoded by the cDNA contained in ATCC Deposit No. 75822.

7. The isolated polypeptide of claim 6 comprising the amino acid sequence of the polypeptide encoded by the cDNA contained in ATCC Deposit No. 75822.

8. The isolated polypeptide of claim 7 consisting of the amino acid sequence of the polypeptide encoded by the cDNA contained in ATCC Deposit No. 75822.

9. An isolated polypeptide produced by a host cell transformed or transfected with a polynucleotide operatively linked to a regulatory element which controls expression wherein said polynucleotide is selected from the group consisting of:

(a) a polynucleotide encoding at least 50 continuous amino acid residues of SEQ ID NO:2;

(b) a polynucleotide encoding amino acid residues 2 to 529 of SEQ ID NO:2;

(c) a polynucleotide encoding amino acid residues 1 to 529 of SEQ ID NO:2;

(d) a polynucleotide encoding at least 50 amino acid residues of the polypeptide encoded by the cDNA contained in ATCC Deposit No. 75822; and (e) a polynucleotide encoding the polypeptide encoded by the cDNA contained in ATCC Deposit No. 75822.

10. The isolated polypeptide of claim 9 wherein said polynucleotide is defined by clause (a).

11. The isolated polypeptide of claim 9 wherein said polynucleotide is defined by clause (b).

12. The isolated polypeptide of claim 9 wherein said polynucleotide is defined by clause (c).

13. The isolated polypeptide of claim 9 wherein said polynucleotide is defined by clause (d).

14. The isolated polypeptide of claim 9 wherein said polynucleotide is defined by clause (e).

* * * * *

UNITED STATES PATENT AND TRADEMARK OFFICE
CERTIFICATE OF CORRECTION

PATENT NO. : 5,994,506
DATED : November 30, 1999
INVENTOR(S) : Daniel R. Soppet, Mark D. Adams, and Yi Li It is certified that error appears in the above-identified patent and that said Letters Patent is hereby corrected as shown below:

On the title page, item [60], third line please delete "PCT/US94/00009" and replace therefor -- PCT/US94/09051 --.

Signed and Sealed this

Twelfth Day of December, 2000

Attest:

Q. TODD DICKINSON

*Attesting Officer*  *Director of Patents and Trademarks*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 2481 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 101..1687

(xi) SEQUENCE DESCRIPTION: SEQ ID NO:1:

```
CCCTCCCAGG TTCAAGCAAT TCTCCGCCTC GGCCTCTCCA GTAGCTGGGA CTACAGTCGT        60

CCAGCATGCT CTGCCCACCC CACGCCGAGG TGCACTGACC ATG AGC CTC AAC TCC        115
                                             Met Ser Leu Asn Ser
                                               1               5

TCC CTC AGC TGC AGG AAG GAG CTG AGT AAT CTC ACT GAG GAG GAG GGT        163
Ser Leu Ser Cys Arg Lys Glu Leu Ser Asn Leu Thr Glu Glu Glu Gly
             10                  15                  20

GGC GAA GGG GCG TCA TCA TCA CCC AGT TCA TCG CCA TCA TTG TCA TCA        211
Gly Glu Gly Ala Ser Ser Ser Pro Ser Ser Pro Ser Leu Ser Ser
             25                  30                  35

CCA TTT TTG TCT GCC TGG GGA AAC CTG GTC ATC GTG GTC ACC TTG TAC        259
Pro Phe Leu Ser Ala Trp Gly Asn Leu Val Ile Val Val Thr Leu Tyr
             40                  45                  50

AAG AAG TCC TAC CTC CTC ACC CTC AGC AAC AAG TTC GTC TTC AGC CTG        307
Lys Lys Ser Tyr Leu Leu Thr Leu Ser Asn Lys Phe Val Phe Ser Leu
     55                  60                  65

ACT CTG TCC AAC TTC CTG CTG TCC GTG TTG GTG CTG CCT TTT GTG GTG        355
Thr Leu Ser Asn Phe Leu Leu Ser Val Leu Val Leu Pro Phe Val Val
 70                  75                  80                  85

ACG AGC TCC ATC CGC AGG GAA TGG ATC TTT GGT GTA GTG TGG TGC AAC        403
Thr Ser Ser Ile Arg Arg Glu Trp Ile Phe Gly Val Val Trp Cys Asn
                 90                  95                 100

TTC TCT GCC CTC CTC TAC CTG CTG ATC AGC TCT GCC AGC ATG CTA ACC        451
Phe Ser Ala Leu Leu Tyr Leu Leu Ile Ser Ser Ala Ser Met Leu Thr
             105                 110                 115

CTC GGG GTC ATT GCC ATC GAC CGC TAC TAT GCT GTC CTG TAC CCC ATG        499
Leu Gly Val Ile Ala Ile Asp Arg Tyr Tyr Ala Val Leu Tyr Pro Met
             120                 125                 130

GTG TAC CCC ATG AAG ATC ACA GGG AAC CGG GCT GTG ATG GCA CTT GTC        547
Val Tyr Pro Met Lys Ile Thr Gly Asn Arg Ala Val Met Ala Leu Val
     135                 140                 145

TAC ATC TGG CTT CAC TCG CTC ATC GGC TGC CTG CCA CCC CTG TTT GGT        595
Tyr Ile Trp Leu His Ser Leu Ile Gly Cys Leu Pro Pro Leu Phe Gly
 150                 155                 160                 165

TGG TCA TCC GTG GAG TAT GGC GAG AAC AAA TGG ATG TGT GTG GCT GCT        643
Trp Ser Ser Val Glu Tyr Gly Glu Asn Lys Trp Met Cys Val Ala Ala
                 170                 175                 180

TGG CAC CGG GAG CCT GGC TAC ACG GCC TTC TGG CAG ATC TGG TGT GCC        691
```

```
Trp His Arg Glu Pro Gly Tyr Thr Ala Phe Trp Gln Ile Trp Cys Ala
            185                 190                 195

CTT TTC CCC TTT CTG GTC ATG CTG GTG TGC TAT GGC TTC ATC TTC CGC        739
Leu Phe Pro Phe Leu Val Met Leu Val Cys Tyr Gly Phe Ile Phe Arg
            200                 205                 210

GTG GCC AGG GTC AAG GCA CGC AAG GTG CAC TGT GGC ACA GTC GTC ATC        787
Val Ala Arg Val Lys Ala Arg Lys Val His Cys Gly Thr Val Val Ile
            215                 220                 225

GTG GAG GAG GAT GCT CAG AGG ACC GGG AGG AAG AAC TCC AGC ACC TCC        835
Val Glu Glu Asp Ala Gln Arg Thr Gly Arg Lys Asn Ser Ser Thr Ser
230                 235                 240                 245

ACC TCC TCT TCA GGG AGG AGG AGG AAT GCC TTT CAG GGT GTG GTC TAC        883
Thr Ser Ser Ser Gly Arg Arg Arg Asn Ala Phe Gln Gly Val Val Tyr
                250                 255                 260

TCG GCC AAC CAG TGC AAA GCC CTC ATC ACC ATC CTG GTG GTC CTC GGT        931
Ser Ala Asn Gln Cys Lys Ala Leu Ile Thr Ile Leu Val Val Leu Gly
                265                 270                 275

GCC TTC ATG GTC ACC TGG GGC CCC TAC ATG GTT GTC ATC GCC TCT GAG        979
Ala Phe Met Val Thr Trp Gly Pro Tyr Met Val Val Ile Ala Ser Glu
                280                 285                 290

GCC CTC TGG GGG AAA AGC TCC GTC TCC CCG AGC CTG GAG ACT TGG GCC       1027
Ala Leu Trp Gly Lys Ser Ser Val Ser Pro Ser Leu Glu Thr Trp Ala
            295                 300                 305

ACA TGG CTG TCC TTT GCC AGC GCT GTC TGC CAC CCC CTG ATC TAT GGA       1075
Thr Trp Leu Ser Phe Ala Ser Ala Val Cys His Pro Leu Ile Tyr Gly
310                 315                 320                 325

CTC TGG AAC AAG ACA GTT CGC AAA GAA CTA CTG GGC ATG TGC TTT GGG       1123
Leu Trp Asn Lys Thr Val Arg Lys Glu Leu Leu Gly Met Cys Phe Gly
                330                 335                 340

GAC CGG TAT TAT CGG GAA CCA TTT GTG CAA CGA CAG AGG ACT TCC AGG       1171
Asp Arg Tyr Tyr Arg Glu Pro Phe Val Gln Arg Gln Arg Thr Ser Arg
                345                 350                 355

CTC TTC AGC ATT TCC AAC AGG ATC ACA GAC CTG GGC CTG TCC CCA CAC       1219
Leu Phe Ser Ile Ser Asn Arg Ile Thr Asp Leu Gly Leu Ser Pro His
                360                 365                 370

CTC ACT GCG CTC ATG GCA GGC GGA CAG CCC CTG GGG CAC AGC AGC AGC       1267
Leu Thr Ala Leu Met Ala Gly Gly Gln Pro Leu Gly His Ser Ser Ser
375                 380                 385

ACG GGG GAC ACT GGC TTC AGC TGC TCC CAG GAC TCA GGG ACA GAT ATG       1315
Thr Gly Asp Thr Gly Phe Ser Cys Ser Gln Asp Ser Gly Thr Asp Met
390                 395                 400                 405

ATG CTG CTT GAG GAC TAC ACG TCT GAT GAC AAC CCT CCC TCT CAC TGC       1363
Met Leu Leu Glu Asp Tyr Thr Ser Asp Asp Asn Pro Pro Ser His Cys
                410                 415                 420

ACT TGC CCA CCC AAG AGA AGG AGC TCG GTG ACA TTT GAG GAT GAA GTG       1411
Thr Cys Pro Pro Lys Arg Arg Ser Ser Val Thr Phe Glu Asp Glu Val
            425                 430                 435

GAA CAA ATC AAA GAA GCT GCC AAG AAC TCG ATT CTT CAT GTG AAA GCT       1459
Glu Gln Ile Lys Glu Ala Ala Lys Asn Ser Ile Leu His Val Lys Ala
            440                 445                 450

GAA GTA CAC AAG TCC TTG GAC AGT TAC GCA GCA AGC TTG GCC AAA GCC       1507
Glu Val His Lys Ser Leu Asp Ser Tyr Ala Ala Ser Leu Ala Lys Ala
            455                 460                 465

ATT GAG GCC GAA GCC AAA ATC AAC TTA TTT GGG GAG GAG GCT TTG CCA       1555
Ile Glu Ala Glu Ala Lys Ile Asn Leu Phe Gly Glu Glu Ala Leu Pro
470                 475                 480                 485

GGG GTC TTG GTT ACA GCA CGG ACT GTC CCG GGG GGC GGC TTC GGG GGC       1603
Gly Val Leu Val Thr Ala Arg Thr Val Pro Gly Gly Gly Phe Gly Gly
            490                 495                 500

CGC CGA GGC AGC AGA ACT CTT GTG AGC CAG AGG CTG CAG TTG CAG AGC       1651
```

```
Arg Arg Gly Ser Arg Thr Leu Val Ser Gln Arg Leu Gln Leu Gln Ser
            505                 510                 515

ATC GAA GAA GGA GAT GTT TTA GCT GCC GAG CAG AGA TGAGGGCCTC         1697
Ile Glu Glu Gly Asp Val Leu Ala Ala Glu Gln Arg
            520                 525

AGGGTGCCGT GGGGCTGCAG CCTGAGAGGC TGGCCCGGGG AGGAGTTCCC ATCACCGCCT  1757

GTGCCGCGGC CTTGGGAGCA TGTCACTGTG TACAGCTGGC CACACACAGG GAAGGAGCAG  1817

CATCTGGTAT GCAGCCACCA GGACAAGGAC TGAAAATAAT GTCTACAGTC CACAGCTTCA  1877

GCATTTCCAG AGACCACATG TGAGCTTCTT TTAGGTCCCA GTGATGGGAC CAGAAGCATC  1937

TAAAGCAAAA AAAAAACCAA AAAAAATTCT AGAGATGTGT TTGTGGCTTT TGGGGAGGTG  1997

GGGCATGGGA GGACCAGAGA CGAAGGGTTT GGAAGGAGAC CCCCACATGC ATCATTTCCT  2057

CCTCTTCACA GTGTGCTGGG AGTCCAGCCG TGCACTGTGC CAGATGCCTC AGGAGGAGAA  2117

CCCTCCCCAG TGTACTGTGA AGGATGAACA CAGAACTTCT TCCTAATGAA ACGCGACCGT  2177

CCTGGTGTCT CTACATGGTT GATGCGGACA GTGTGGGACC CTCAGTTCTA GGACTGGTCC  2237

GCAGAGAATT TACCCAGGTG CAGTGCGCTT CGGAGCGGTC CTCAGTGGCG GCACCTGTTG  2297

GTGTTAATAG GGACAGACAC AGGCCTCTTG CAGTCTGGAC CACCCTGTCT ACTTCCCTAC  2357

TTAAAAGGTC TTGGGTATTT CAAAAGGGAG AAACCACTTA TAATAGTGAA GTTGGTAGGG  2417

CAGTACTACT CTGTTTCATT TCCAGAATTA AAAAAAAAAT AAATATTATT CCTGCGGCCT  2477

GTTA                                                               2481

(2) INFORMATION FOR SEQ ID NO:2:

(i) SEQUENCE CHARACTERISTICS:
        (A) LENGTH: 529 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Leu Asn Ser Ser Leu Ser Cys Arg Lys Glu Leu Ser Asn Leu
 1               5                  10                  15

Thr Glu Glu Gly Gly Glu Gly Ala Ser Ser Pro Ser Ser
            20                  25                  30

Pro Ser Leu Ser Ser Pro Phe Leu Ser Ala Trp Gly Asn Leu Val Ile
            35                  40                  45

Val Val Thr Leu Tyr Lys Lys Ser Tyr Leu Leu Thr Leu Ser Asn Lys
         50                  55                  60

Phe Val Phe Ser Leu Thr Leu Ser Asn Phe Leu Leu Ser Val Leu Val
 65                  70                  75                  80

Leu Pro Phe Val Val Thr Ser Ser Ile Arg Arg Glu Trp Ile Phe Gly
                    85                  90                  95

Val Val Trp Cys Asn Phe Ser Ala Leu Leu Tyr Leu Leu Ile Ser Ser
                100                 105                 110

Ala Ser Met Leu Thr Leu Gly Val Ile Ala Ile Asp Arg Tyr Tyr Ala
            115                 120                 125

Val Leu Tyr Pro Met Val Tyr Pro Met Lys Ile Thr Gly Asn Arg Ala
        130                 135                 140

Val Met Ala Leu Val Tyr Ile Trp Leu His Ser Leu Ile Gly Cys Leu
145                 150                 155                 160

Pro Pro Leu Phe Gly Trp Ser Ser Val Glu Tyr Gly Glu Asn Lys Trp
                165                 170                 175
```

Met Cys Val Ala Ala Trp His Arg Glu Pro Gly Tyr Thr Ala Phe Trp
            180                 185                 190

Gln Ile Trp Cys Ala Leu Phe Pro Phe Leu Val Met Leu Val Cys Tyr
        195                 200                 205

Gly Phe Ile Phe Arg Val Ala Arg Val Lys Ala Arg Lys Val His Cys
        210                 215                 220

Gly Thr Val Val Ile Val Glu Glu Asp Ala Gln Arg Thr Gly Arg Lys
225                 230                 235                 240

Asn Ser Ser Thr Ser Thr Ser Ser Ser Gly Arg Arg Asn Ala Phe
                245                 250                 255

Gln Gly Val Val Tyr Ser Ala Asn Gln Cys Lys Ala Leu Ile Thr Ile
                260                 265                 270

Leu Val Val Leu Gly Ala Phe Met Val Thr Trp Gly Pro Tyr Met Val
        275                 280                 285

Val Ile Ala Ser Glu Ala Leu Trp Gly Lys Ser Val Ser Pro Ser
290                 295                 300

Leu Glu Thr Trp Ala Thr Trp Leu Ser Phe Ala Ser Ala Val Cys His
305                 310                 315                 320

Pro Leu Ile Tyr Gly Leu Trp Asn Lys Thr Val Arg Lys Glu Leu Leu
                325                 330                 335

Gly Met Cys Phe Gly Asp Arg Tyr Tyr Arg Glu Pro Phe Val Gln Arg
                340                 345                 350

Gln Arg Thr Ser Arg Leu Phe Ser Ile Ser Asn Arg Ile Thr Asp Leu
            355                 360                 365

Gly Leu Ser Pro His Leu Thr Ala Leu Met Ala Gly Gly Pro Leu
        370                 375                 380

Gly His Ser Ser Ser Thr Gly Asp Thr Gly Phe Ser Cys Ser Gln Asp
385                 390                 395                 400

Ser Gly Thr Asp Met Met Leu Leu Glu Asp Tyr Thr Ser Asp Asp Asn
                405                 410                 415

Pro Pro Ser His Cys Thr Cys Pro Pro Lys Arg Arg Ser Ser Val Thr
                420                 425                 430

Phe Glu Asp Glu Val Glu Gln Ile Lys Glu Ala Ala Lys Asn Ser Ile
            435                 440                 445

Leu His Val Lys Ala Glu Val His Lys Ser Leu Asp Ser Tyr Ala Ala
        450                 455                 460

Ser Leu Ala Lys Ala Ile Glu Ala Glu Ala Lys Ile Asn Leu Phe Gly
465                 470                 475                 480

Glu Glu Ala Leu Pro Gly Val Leu Val Thr Ala Arg Thr Val Pro Gly
                485                 490                 495

Gly Gly Phe Gly Gly Arg Arg Gly Ser Arg Thr Leu Val Ser Gln Arg
                500                 505                 510

Leu Gln Leu Gln Ser Ile Glu Glu Gly Asp Val Leu Ala Ala Glu Gln
            515                 520                 525

Arg (2) INFORMATION FOR SEQ ID NO:3:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CCCACCCCAC GCCGAGGTGC AGGTGCAGGA TCCATGAGCC TCAAC                45
```

(2) INFORMATION FOR SEQ ID NO:4:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CAGCCCCACG GCACCCTCTA GACCTCATCT CTGCTCGGCA GCT                  43
```

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CCCACCCCAC GCCGGGATCC ACTGACCATG                                 30
```

(2) INFORMATION FOR SEQ ID NO:6:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
CCGCTCGAGC CTTCAAGCGT AGTCTGGGAC GTCGTATGGG TATCTCTGCT CGGCAGC   57
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CCCACCCCAC GCCGGGATCC ACTGACCATG                                 30
```

(2) INFORMATION FOR SEQ ID NO:8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CAGCCCCACG GCACCCTCTA GACCTCATCT CTGCTCGGCA GCT                  43
```

(2) INFORMATION FOR SEQ ID NO:9:

(i) SEQUENCE CHARACTERISTICS:
    (A) LENGTH: 501 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:9:

```
Met Ala Ala Ala Leu Arg Ser Val Met Met Ala Gly Tyr Leu Ser Glu
1               5                   10                  15

Trp Arg Thr Pro Thr Tyr Arg Ser Thr Glu Met Val Gln Arg Leu Arg
            20                  25                  30

Met Glu Ala Val Gln His Ser Thr Ser Thr Ala Ala Val Gly Gly Leu
        35                  40                  45

Val Val Ser Ala Gln Gly Val Gly Val Gly Val Phe Leu Ala Ala Phe
    50                  55                  60

Ile Leu Met Ala Val Ala Gly Asn Leu Leu Val Ile Leu Ser Val Ala
65              70                  75                  80

Cys Asn Arg His Leu Gln Thr Val Thr Asn Tyr Phe Ile Val Asn Leu
                85                  90                  95

Ala Val Ala Asp Leu Leu Leu Ser Ala Thr Val Leu Pro Phe Ser Ala
            100                 105                 110

Thr Met Glu Val Leu Gly Phe Trp Ala Phe Gly Arg Ala Phe Cys Asp
        115                 120                 125

Val Trp Ala Ala Val Asp Val Leu Cys Cys Thr Ala Ser Ile Leu Ser
    130                 135                 140

Leu Cys Thr Ile Ser Val Asp Arg Tyr Val Gly Val Arg His Ser Leu
145                 150                 155                 160

Lys Tyr Pro Ala Ile Met Thr Glu Arg Lys Ala Ala Ala Ile Leu Ala
                165                 170                 175

Leu Leu Trp Val Val Ala Leu Val Val Ser Val Gly Pro Leu Leu Gly
            180                 185                 190

Trp Lys Glu Pro Val Pro Pro Asp Glu Arg Phe Cys Gly Ile Thr Glu
        195                 200                 205

Glu Ala Gly Tyr Ala Val Phe Ser Ser Val Cys Ser Phe Tyr Leu Pro
    210                 215                 220

Met Ala Val Ile Val Val Met Tyr Cys Arg Val Tyr Val Val Ala Arg
225                 230                 235                 240

Ser Thr Thr Arg Ser Leu Glu Ala Gly Val Lys Arg Glu Arg Gly Lys
                245                 250                 255

Ala Ser Glu Val Val Leu Arg Ile His Cys Arg Gly Ala Ala Thr Gly
            260                 265                 270

Ala Asp Gly Ala His Gly Met Arg Ser Ala Lys Gly His Thr Phe Arg
        275                 280                 285

Ser Ser Leu Ser Val Arg Leu Leu Lys Phe Ser Arg Glu Lys Lys Ala
    290                 295                 300

Ala Lys Thr Leu Ala Ile Val Val Gly Val Phe Val Leu Cys Trp Phe
305                 310                 315                 320

Pro Phe Phe Phe Val Leu Pro Leu Gly Ser Leu Phe Pro Gln Leu Lys
                325                 330                 335

Pro Ser Glu Gly Val Phe Lys Val Ile Phe Trp Leu Gly Tyr Phe Asn
            340                 345                 350

Ser Cys Val Asn Pro Leu Ile Tyr Pro Cys Ser Ser Arg Glu Phe Lys
        355                 360                 365
```

```
Arg Ala Phe Leu Arg Leu Leu Arg Cys Gln Cys Arg Arg Arg Arg
    370                 375                 380

Arg Arg Pro Leu Trp Arg Val Tyr Gly His His Trp Arg Ala Ser Thr
385                 390                 395                 400

Ser Gly Leu Arg Gln Asp Cys Ala Pro Ser Ser Gly Asp Ala Pro Pro
                405                 410                 415

Gly Ala Pro Leu Ala Leu Thr Ala Leu Pro Asp Pro Asp Pro Glu Pro
                420                 425                 430

Pro Gly Thr Pro Glu Met Gln Ala Pro Val Ala Ser Arg Arg Ser His
                435                 440                 445

Pro Ala Pro Ser Ala Ser Gly Gly Cys Trp Gly Arg Ser Gly Asp Pro
            450                 455                 460

Arg Pro Ser Cys Ala Pro Lys Ser Pro Ala Cys Arg Thr Arg Ser Pro
465                 470                 475                 480

Pro Gly Ala Arg Ser Ala Gln Arg Gln Arg Ala Pro Ser Ala Gln Arg
                485                 490                 495

Trp Arg Leu Cys Pro
                500
```

(2) INFORMATION FOR SEQ ID NO:10:

(i) SEQUENCE CHARACTERISTICS:
        (A) LENGTH: 517 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Asn Pro Asp Leu Asp Thr Gly His Asn Thr Ser Ala Pro Ala His
1               5                   10                  15

Trp Gly Glu Leu Lys Asn Ala Asn Phe Thr Gly Pro Asn Gln Thr Ser
                20                  25                  30

Ser Asn Ser Thr Leu Pro Gln Leu Asp Ile Thr Arg Ala Ile Ser Val
            35                  40                  45

Gly Leu Val Leu Gly Ala Phe Ile Leu Phe Ala Ile Val Gly Asn Ile
50                  55                  60

Leu Val Ile Leu Ser Val Ala Cys Asn Arg His Leu Arg Thr Pro Thr
65                  70                  75                  80

Asn Tyr Phe Ile Val Asn Leu Ala Met Ala Asp Leu Leu Leu Ser Phe
                85                  90                  95

Thr Val Leu Pro Phe Ser Ala Ala Leu Glu Val Leu Gly Tyr Trp Val
                100                 105                 110

Leu Gly Arg Ile Phe Cys Asp Ile Trp Ala Ala Val Asp Val Leu Cys
            115                 120                 125

Cys Thr Ala Ser Ile Leu Ser Leu Cys Ala Ile Ser Ile Asp Arg Tyr
130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
            195                 200                 205

Leu Gly Ser Phe Tyr Ile Pro Leu Ala Val Ile Leu Val Met Tyr Cys
```

```
            210                 215                 220
Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                245                 250                 255

Ser Lys Asn Phe His Glu Asp Thr Leu Ser Ser Thr Lys Ala Lys Gly
                260                 265                 270

His Asn Pro Arg Ser Ser Ile Ala Val Lys Leu Phe Lys Phe Ser Arg
                275                 280                 285

Glu Lys Lys Ala Ala Lys Thr Leu Gly Ile Val Val Gly Met Phe Ile
                290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                325                 330                 335

Gly Tyr Phe Asn Ser Cys Leu Asn Pro Ile Ile Tyr Pro Cys Ser Ser
                340                 345                 350

Lys Glu Phe Lys Arg Ala Phe Val Arg Ile Leu Gly Cys Gln Cys Arg
                355                 360                 365

Gly Arg Arg Arg Arg Arg Arg Arg Arg Leu Gly Gly Cys Ala Tyr
                370                 375                 380

Thr Tyr Arg Pro Trp Thr Arg Gly Gly Ser Leu Glu Arg Ser Gln Ser
385                 390                 395                 400

Arg Lys Asp Ser Leu Asp Asp Ser Gly Ser Cys Leu Ser Gly Ser Gln
                405                 410                 415

Arg Thr Leu Pro Ser Ala Ser Pro Ser Pro Gly Tyr Leu Gly Arg Gly
                420                 425                 430

Ala Pro Pro Pro Val Glu Leu Cys Ala Phe Pro Glu Trp Lys Ala Pro
                435                 440                 445

Gly Ala Leu Leu Ser Leu Pro Ala Pro Glu Pro Gly Arg Arg Gly
450                 455                 460

Arg His Asp Ser Gly Pro Leu Phe Thr Phe Lys Leu Leu Thr Glu Pro
465                 470                 475                 480

Glu Ser Pro Gly Thr Asp Gly Gly Ala Ser Asn Gly Gly Cys Glu Pro
                485                 490                 495

Arg His Val Ala Asn Gly Gln Pro Gly Phe Lys Ser Asn Met Pro Leu
                500                 505                 510

Ala Pro Gly Gln Phe
                515

(2) INFORMATION FOR SEQ ID NO:11:

(i) SEQUENCE CHARACTERISTICS:
        (A) LENGTH: 466 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Val Phe Leu Ser Gly Asn Ala Ser Asp Ser Ser Asn Cys Thr Gln
1               5                   10                  15

Pro Pro Ala Pro Val Asn Ile Ser Lys Ala Ile Leu Leu Gly Val Ile
                20                  25                  30

Leu Gly Gly Leu Ile Leu Phe Gly Val Leu Gly Asn Ile Leu Val Ile
                35                  40                  45
```

-continued

```
Leu Ser Val Ala Cys His Arg His Leu His Ser Val Thr His Tyr Tyr
     50                      55                      60
Ile Val Asn Leu Ala Val Ala Asp Leu Leu Thr Ser Thr Val Leu
 65                      70                      75                      80
Pro Phe Ser Ala Ile Phe Glu Val Leu Gly Tyr Trp Ala Phe Gly Arg
                      85                      90                      95
Val Phe Cys Asn Ile Trp Ala Ala Val Asp Val Leu Cys Cys Thr Ala
                     100                     105                     110
Ser Ile Met Gly Leu Cys Ile Ile Ser Ile Asp Arg Tyr Ile Gly Val
                     115                     120                     125
Ser Tyr Pro Leu Arg Tyr Pro Thr Ile Val Thr Gln Arg Arg Gly Leu
                     130                     135                     140
Met Ala Leu Leu Cys Val Trp Ala Leu Ser Leu Val Ile Ser Ile Gly
145                     150                     155                     160
Pro Leu Phe Gly Trp Arg Gln Pro Ala Pro Glu Asp Glu Thr Ile Cys
                     165                     170                     175
Gln Ile Asn Glu Glu Pro Gly Tyr Val Leu Phe Ser Ala Leu Gly Ser
                     180                     185                     190
Phe Tyr Leu Pro Leu Ala Ile Ile Leu Val Met Tyr Cys Arg Val Tyr
                     195                     200                     205
Val Val Ala Lys Arg Glu Ser Arg Gly Leu Lys Ser Gly Leu Lys Thr
                     210                     215                     220
Asp Lys Ser Asp Ser Glu Gln Val Thr Leu Arg Ile His Arg Lys Asn
225                     230                     235                     240
Ala Pro Ala Gly Gly Ser Gly Met Ala Ser Ala Lys Thr Lys Thr His
                     245                     250                     255
Phe Ser Val Arg Leu Leu Lys Phe Ser Arg Glu Lys Lys Ala Ala Lys
                     260                     265                     270
Thr Leu Gly Ile Val Val Gly Cys Phe Val Leu Cys Trp Leu Pro Phe
                     275                     280                     285
Phe Leu Val Met Pro Ile Gly Ser Phe Phe Pro Asp Phe Lys Pro Ser
                     290                     295                     300
Glu Thr Val Phe Lys Ile Val Phe Trp Leu Gly Tyr Leu Asn Ser Cys
305                     310                     315                     320
Ile Asn Pro Ile Ile Tyr Pro Cys Ser Ser Gln Glu Phe Lys Lys Ala
                     325                     330                     335
Phe Gln Asn Val Leu Arg Ile Gln Cys Leu Arg Arg Lys Gln Ser Ser
                     340                     345                     350
Lys His Ala Leu Gly Tyr Thr Leu His Pro Pro Ser Gln Ala Val Glu
                     355                     360                     365
Gly Gln His Lys Asp Met Val Arg Ile Pro Val Gly Ser Arg Glu Thr
                     370                     375                     380
Phe Tyr Arg Ile Ser Lys Thr Asp Gly Val Cys Glu Trp Lys Phe Phe
385                     390                     395                     400
Ser Ser Met Pro Arg Gly Ser Ala Arg Ile Thr Val Ser Lys Asp Gln
                     405                     410                     415
Ser Ser Cys Thr Thr Ala Arg Val Arg Ser Lys Ser Phe Leu Glu Val
                     420                     425                     430
Cys Cys Cys Val Gly Pro Ser Thr Pro Ser Leu Asp Lys Asn His Gln
                     435                     440                     445
Val Pro Thr Ile Lys Val His Thr Ile Ser Leu Ser Glu Asn Gly Glu
450                     455                     460

Glu Val
```

465

(2) INFORMATION FOR SEQ ID NO:12:

(i) SEQUENCE CHARACTERISTICS:
        (A) LENGTH: 413 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Gly Gln Pro Gly Asn Gly Ser Ala Phe Leu Leu Ala Pro Asn Arg
 1               5                  10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
 50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350
```

Gly Tyr Ser Ser Asn Gly Asn Thr Gly Glu Gln Ser Gly Tyr His Val
            355                 360                 365

Glu Gln Glu Lys Glu Asn Lys Leu Leu Cys Glu Asp Leu Pro Gly Thr
        370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
            405                 410

(2) INFORMATION FOR SEQ ID NO:13:

(i) SEQUENCE CHARACTERISTICS:
        (A) LENGTH: 359 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Met Ala Pro Asn Gly Thr Ala Ser Ser Phe Cys Leu Asp Ser Thr Ala
1               5                   10                  15

Cys Lys Ile Thr Ile Thr Val Val Leu Ala Val Leu Ile Leu Ile Thr
            20                  25                  30

Val Ala Gly Asn Val Val Val Cys Leu Ala Val Gly Leu Asn Arg Arg
            35                  40                  45

Leu Arg Asn Leu Thr Asn Cys Phe Ile Val Ser Leu Ala Ile Thr Asp
        50                  55                  60

Leu Leu Leu Gly Leu Leu Val Leu Pro Phe Ser Ala Ile Tyr Gln Leu
65                  70                  75                  80

Ser Cys Lys Trp Ser Phe Gly Lys Val Phe Cys Asn Ile Tyr Thr Ser
            85                  90                  95

Leu Asp Val Met Leu Cys Thr Ala Ser Ile Leu Asn Leu Phe Met Ile
            100                 105                 110

Ser Leu Asp Arg Tyr Cys Ala Val Met Asp Pro Leu Arg Tyr Pro Val
            115                 120                 125

Leu Val Thr Pro Val Arg Val Ala Ile Ser Leu Val Leu Ile Trp Val
        130                 135                 140

Ile Ser Ile Thr Leu Ser Phe Leu Ser Ile His Leu Gly Trp Asn Ser
145                 150                 155                 160

Arg Asn Glu Thr Ser Lys Gly Asn His Thr Thr Ser Lys Cys Lys Val
            165                 170                 175

Gln Val Asn Glu Val Tyr Gly Leu Val Asp Gly Leu Val Thr Phe Tyr
            180                 185                 190

Leu Pro Leu Leu Ile Met Cys Ile Thr Tyr Tyr Arg Ile Phe Lys Val
        195                 200                 205

Ala Arg Asp Gln Ala Lys Arg Ile Asn His Ile Ser Ser Trp Lys Ala
210                 215                 220

Ala Thr Ile Arg Glu His Lys Ala Thr Val Thr Leu Ala Ala Val Met
225                 230                 235                 240

Gly Ala Phe Ile Ile Cys Trp Phe Pro Tyr Phe Thr Ala Phe Val Tyr
            245                 250                 255

Arg Gly Leu Arg Gly Asp Asp Ala Ile Asn Glu Val Leu Glu Ala Ile
            260                 265                 270

Val Leu Trp Leu Gly Tyr Ala Asn Ser Ala Leu Asn Pro Ile Leu Tyr
        275                 280                 285

```
Ala Ala Leu Asn Arg Asp Phe Arg Thr Gly Tyr Gln Gln Leu Phe Cys
    290                 295                 300

Cys Arg Leu Ala Asn Arg Asn Ser His Lys Thr Ser Leu Arg Ser Asn
305                 310                 315                 320

Ala Ser Gln Leu Ser Arg Thr Gln Ser Arg Glu Pro Arg Gln Gln Glu
                325                 330                 335

Glu Lys Pro Leu Lys Leu Gln Val Trp Ser Gly Thr Glu Val Thr Ala
            340                 345                 350

Pro Gln Gly Ala Thr Asp Arg
        355
```